US012714585B2

(12) United States Patent
Ding et al.

(10) Patent No.: US 12,714,585 B2
(45) Date of Patent: *Aug. 25, 2026

(54) STENT, STENT KIT, AND STENT DELIVERY SYSTEM

(71) Applicant: SHANGHAI FLOWDYNAMICS MEDICAL TECHNOLOGY CO., LTD., Shanghai (CN)

(72) Inventors: Jian Ding, Shanghai (CN); Chenying Fan, Shanghai (CN)

(73) Assignee: SHANGHAI FLOWDYNAMICS MEDICAL TECHNOLOGY CO., LTD., Shanghai (CN)

(*) Notice: Subject to any disclaimer, the term of this patent is extended or adjusted under 35 U.S.C. 154(b) by 819 days.

This patent is subject to a terminal disclaimer.

(21) Appl. No.: 18/003,891

(22) PCT Filed: Nov. 6, 2020

(86) PCT No.: PCT/CN2020/127273

§ 371 (c)(1),
(2) Date: Dec. 29, 2022

(87) PCT Pub. No.: WO2022/007281

PCT Pub. Date: Jan. 13, 2022

(65) Prior Publication Data

US 2023/0255804 A1 Aug. 17, 2023

(30) Foreign Application Priority Data

Jul. 6, 2020 (CN) ......................... 202010642761.2

(51) Int. Cl.
*A61F 2/90* (2013.01)
*A61F 2/86* (2013.01)
(Continued)

(52) U.S. Cl.
CPC .................. *A61F 2/90* (2013.01); *A61F 2/86* (2013.01); *A61F 2/88* (2013.01); *A61F 2002/823* (2013.01); *A61F 2210/0066* (2013.01)

(58) Field of Classification Search
CPC ...... A61F 2/04; A61F 2/07; A61F 2/82; A61F 2/86; A61F 2/88; A61F 2/885; A61F 2/90;
(Continued)

(56) References Cited

U.S. PATENT DOCUMENTS

| | | | |
|---|---|---|---|
| 6,015,432 | A | 1/2000 | Rakos |
| 10,470,904 | B2 | 11/2019 | Folan |

(Continued)

FOREIGN PATENT DOCUMENTS

| | | | |
|---|---|---|---|
| CN | 1479597 | A | 3/2004 |
| CN | 102727332 | A | 10/2012 |

(Continued)

OTHER PUBLICATIONS

Supplementary European Search Report in the European application No. 20943874.6, mailed on Jun. 24, 2024. 8 pages.

(Continued)

*Primary Examiner* — Dinah Baria
(74) *Attorney, Agent, or Firm* — Syncoda LLC; Feng Ma

(57) ABSTRACT

A stent, for use in an aorta, is characterized in that the stent is at least made of a first wire and a second wire of different diameters by means of weaving, and the stent is configured to be at least partially compressible and extensible in the axial direction of the stent in a natural release state, wherein the first wire has a diameter of 20-150 μm, and the second wire has a diameter of 150-800 μm. When the stent is used in the treatment of aortic aneurysm lesions and/or aortic dissection lesions, the stent provides low fluid permeability
(Continued)

and a strong radial support force at the desired site in the aorta by means of the axial compressibility and extensibility of the stent, and is easily assembled into the delivery system having a suitable diameter. Further provided are the stent kit comprising the stent, and the stent delivery system.

16 Claims, 5 Drawing Sheets

(51) Int. Cl.
*A61F 2/88* (2006.01)
*A61F 2/82* (2013.01)

(58) Field of Classification Search
CPC .......... A61F 2002/823; A61F 2002/068; A61F 2250/0007; A61F 2250/0012; A61F 2250/0023; A61F 2250/0024; A61F 2250/0039
See application file for complete search history.

(56) References Cited

U.S. PATENT DOCUMENTS

| | | | | |
|---|---|---|---|---|
| 2001/0056299 | A1 | 12/2001 | Thompson | |
| 2003/0100945 | A1* | 5/2003 | Yodfat | A61F 2/82 623/1.53 |
| 2006/0190070 | A1 | 8/2006 | Dieck | |
| 2007/0168019 | A1 | 7/2007 | Amplatz | |
| 2010/0161025 | A1 | 6/2010 | Kuppurathanam | |
| 2017/0100231 | A1* | 4/2017 | Frid | A61F 2/852 |
| 2017/0333230 | A1 | 11/2017 | Folan et al. | |
| 2019/0223879 | A1 | 7/2019 | Jayaraman | |
| 2020/0046528 | A1 | 2/2020 | Folan et al. | |
| 2021/0137715 | A1* | 5/2021 | Ringwala | A61F 2/966 |

FOREIGN PATENT DOCUMENTS

| | | | |
|---|---|---|---|
| CN | 103561682 | A | 2/2014 |
| CN | 104042296 | A | 9/2014 |
| CN | 203885667 | U | 10/2014 |
| CN | 104689379 | A | 6/2015 |
| CN | 104720941 | A | 6/2015 |
| CN | 105125326 | A | 12/2015 |
| CN | 105228561 | A | 1/2016 |
| CN | 107106286 | A | 8/2017 |
| CN | 207400830 | U | 5/2018 |
| CN | 109890323 | A | 6/2019 |
| CN | 109966018 | A | 7/2019 |
| CN | 110013372 | A | 7/2019 |
| CN | 110234296 | A | 9/2019 |
| CN | 209347136 | U | 9/2019 |
| CN | 107427374 | B | 10/2019 |
| CN | 110353866 | A | 10/2019 |
| CN | 110731843 | A | 1/2020 |
| CN | 212662039 | U | 3/2021 |
| EP | 1946721 | A1 | 7/2008 |
| JP | H1033692 | A | 2/1998 |
| JP | H10328216 | A | 12/1998 |
| JP | 2004520101 | A | 7/2004 |
| JP | 2004528862 | A | 9/2004 |
| JP | 2012523922 | A | 10/2012 |
| JP | 2012223209 | A | 11/2012 |
| JP | 2017511742 | A | 4/2017 |
| JP | 2018000794 | A | 1/2018 |

OTHER PUBLICATIONS

International Search Report in the international application No. PCT/CN2020/127273, mailed on Mar. 30, 2021.

Written Opinion of the International Search Authority in the international application No. PCT/CN2020/127273, mailed on Mar. 30, 2021.

International Search Report in the international application No. PCT /CN2020/127259, mailed on Apr. 2, 2021.

English translation of the Written Opinion of the International Search Authority in the international application No. PCT /CN2020/ 127259, mailed on Apr. 6, 2021.

Supplementary European Search Report in the European application No. 20944499.1, mailed on Jul. 5, 2024.

* cited by examiner

STENT, STENT KIT, AND STENT DELIVERY SYSTEM

CROSS-REFERENCE TO RELATED APPLICATIONS

This application is a National Stage of International Patent Application No. PCT/CN2020/127273 filed on Nov. 6, 2020, which claims priority to Chinese Patent Application No. 202010642761.2 filed on Jul. 6, 2020. The disclosures of the above-referenced applications are hereby incorporated by reference in their entirety.

TECHNICAL FIELD

The disclosure relates to a stent, a stent kit, a stent delivery system, and a method for placing a stent by a stent delivery system, and in particular to a stent, a stent kit, and a system and method for delivering and placing a stent, which are used in treatment of aortic lesions, such as aortic aneurysm or aortic dissection.

BACKGROUND

The arterial vessel wall is formed by tightly fitting an intima, a tunica media and an adventitia. When an inner wall of the arterial vessel is partially damaged, the tunica media of the arterial vessel wall is gradually peeled off under a strong impact of arterial blood flow, so that blood enters between the tunica media and the adventitia of the vessel wall, thereby forming two lumens, i.e., a true lumen and a false lumen. The most common type is aortic dissection. The aortic dissection weakens the arterial wall, so that there is a risk of rupture of the aortic dissection at any time. Once the dissection ruptures, the patient will die in several minutes.

The aortic dissection is divided into two types, i.e., type A and type B (i.e., Stanford classification) according to an intima tearing site and an expansion range. Type A refers to a lesion involving an ascending aorta, which refers to a situation in which a peeling site of the arterial wall starts from the ascending aorta, and the lesion may also occur at an aortic arch or a proximal end of a descending aorta involving the ascending aorta. Type B refers to a situation in which a peeling site of the arterial wall occurs at the descending aorta without extending beyond a proximal end of an opening of a left subclavian artery.

The aortic aneurysm is also a disease in which an aorta is abnormally dilated. Rupture of the aortic aneurysm is also fatal for the patient.

Therefore, early diagnosis and timely treatment of the aortic dissection and the aortic aneurysm are essential.

At present, there are usually three solutions for treating the aortic dissection or the aortic aneurysm.

One solution is to use an open surgery through artificial vessel replacement. At present, this solution is mostly used for type A aortic dissection, and has the defects that the intraoperative mortality is high, a residual dissection is often formed after the surgery (that is, type B dissection is formed), and the re-operation rate within 10 years is up to 9%-67%. Furthermore, with this solution, the treatment cost is very high, and there are relatively few hospitals that have mastered this surgical technique. In addition, the open surgery is not suitable for all patients, thus, a very small proportion of patients may benefit from this solution.

Another solution is the EVAR endovascular intervention, i.e., a covered stent implantation. This solution has advantages of less trauma, rapid recovery and low mortality. However, the stent placement site often involves the aortic arch and/or the abdominal aorta, three branch artery vessels at the convex side of the aortic arch, as well as the major branch artery vessels at the abdominal aorta, such as the left renal artery, the right renal artery, the coeliac trunk and the superior mesenteric artery, cannot be obstructed throughout the surgery and after the surgery. Thus, the conventional practice is to perform the on-site drilling at a site of the covered stent corresponding to an important branch artery. On the one hand, difficulty of surgery is increased, so that the surgery needs to be performed by an experienced surgeon. On the other hand, once positioning of the stent is inaccurate during placement, or the stent is displaced during release, an important branch vessel may be obstructed, which may induce serious consequences. Furthermore, the stent is modified before surgery, and thus the manufacturer thereof may refuse to provide a warranty service for this reason.

A third solution is a recently proposed solution for performing total aortic endovascular intervention by using a dense mesh stent. Unlike the EVAR endovascular intervention, in this solution, the mechanism of mechanically obstructing the false lumen is not used, and the dense mesh stent does not significantly hinder passage of blood flow. Instead, in this solution, by creating an obstruction to blood flow at the inner wall of the lesion vessel, the hemodynamics in the false lumen is changed, the pressure in the false lumen is reduced, and the intraluminal thrombus is promoted, thereby achieving the therapeutic purposes. Due to the use of the dense mesh stent, compared with the EVAR endovascular intervention, this solution has advantages of less trauma, rapid recovery and low mortality, and the dense mesh stent does not significantly obstruct the blood flow to the branch arteries, thereby greatly reducing the difficulty of surgery. Therefore, this solution may be performed by a doctor with ordinary experience.

However, the treatment effect of this type of stent is not satisfactory. Since the tear of the inner wall of the blood vessel is not completely obstructed, an ideal intraluminal thrombus cannot be always formed. Furthermore, the existing dense mesh stents are still difficult to be applied to all lesion types of aortic dissection and aortic aneurysm, especially difficult to be applied to type A aortic lesion.

Type A aortic dissection involves the ascending aorta, and an inner diameter of the blood vessel at this site is significantly increased due to the lesion, usually up to 38-55 cm. A dense mesh stent with such a large diameter cannot be radially compressed to stent with a very small diameter, and thus a thicker delivery system is often needed. In this case, the delivery system is difficult to be placed through a femoral artery with a relatively small diameter, even the delivery system is unable to be placed especially in Asian people with relatively thinner blood vessels. In order to reduce the diameter of the stent in a compressed state, thinner wires may be used to weave the stent. However, this results in that the radial support force of the stent is insufficient to achieve the therapeutic purposes.

SUMMARY

In view of this, a main purpose of the disclosure is to provide a stent, a stent kit, a delivery system including such a stent, and a stent placement method, which are capable of solving or improving at least one of the above problems in the related art. Specifically, a purpose of the disclosure is to provide a stent, which has a diameter suitable for delivering the stent through a femoral artery in a delivery state, and which is configured to treat the aortic dissection or the aortic aneurysm, especially type A aortic lesion. The stent may be partially compressed axially in a release state, thereby forming a segment with low liquid permeability and high radial support force at a desired site (such as the ascending aorta), thereby achieving the treatment of the lesion site.

To this end, a first aspect of the disclosure provides a stent. The stent is used in an aorta. The stent is formed by weaving at least two kinds of wires with different diameters, and the stent is configured to be at least partially compressible and extendable along an axial direction of the stent in a release state. A diameter of a first wire ranges from 20 μm to 150 μm, and a diameter of a second wire ranges from 150 μm to 800 μm.

The stent in the disclosure is at least partially compressible and extendable axially in the release state, especially according to a stent delivery system and a stent placement method as described in detail below. On the one hand, when the stent is released in the blood vessel, a density of woven wires is significantly increased in a local segment of the stent by partially axial compression, thereby substantially obtaining a desired liquid impermeability to obstruct a tear and obtaining a radial support force for expanding a true lumen. Especially at a tearing site of the vessel intima, more particularly in the ascending aorta, the partially enhanced radial support force and the significantly reduced fluid (blood) permeability may be obtained by axially compressing the stent that has been partially released. On the other hand, due to the above characteristics, if necessary, the stent may be axially extended to allow the density of the woven wires to be significantly reduced, and then the stent is radially compressed, so that the stent is easily compressed into a delivery configuration with a suitable diameter, and may be conveniently assembled into the delivery system as described in detail below. Furthermore, at a site where a branch artery is present, if necessary, the meshes of the stent may become sparse through partially axial extension, thereby facilitating delivery of blood to the branch artery, and facilitating placement of a branch stent through the aperture if necessary.

The stent in the disclosure is formed by weaving at least two kinds of wires with different diameters. On the one hand, this enables a large-sized stent used in the aorta to have a moderate radial support force and metal coverage, and to be radially compressed to a suitable delivery dimension. On the other hand, the thicker second wires form a basic support skeleton and provide a basic radial support force, and the thinner first wires may effectively fill gaps between the second wires and provide an ancillary support and maintain the morphology of the stent. In particular, after the stent is axially compressed, due to the presence of the first wires, the fluid permeability of the compressed portion may be significantly reduced to form an effective obstruction on a tearing site of an inner wall of the blood vessel. Meanwhile, after the thicker second wires are axially compressed, the density of the second wires per unit length is increased, so that a significantly enhanced radial support force may be formed, thereby expanding the true lumen of the blood vessel and facilitating reduction of the false lumen.

According to an embodiment, in a natural release state (i.e., without subjected to axial compression and without extension), a metal coverage of the stent is at least 30%, and a radial support force of the stent is greater than or equal to 100 N.

Preferably, in the natural release state, the metal coverage of the stent ranges from 30% to 90%, and the radial support force of the stent ranges from 100 N to 600 N.

According to an embodiment, in a release and axial maximum compression state, a metal coverage of the stent is at least 80%, and a radial support force of the stent is greater than or equal to 400 N. Preferably, in the release and axial maximum compression state, the metal coverage of the stent ranges from 80% to 100%, and the radial support force of the stent ranges from 400 N to 1000 N.

In a range of the radial support force in the natural release state as defined above, the stent in the disclosure may be easily assembled into a delivery system with a suitable outer diameter (e.g., 5-10 mm) even with a maximum diameter (such as 38-60 mm) suitable for the ascending aorta. Furthermore, after the stent is compressed to the maximum along the axial direction, the stent having a radial support force in the above range may effectively support a narrowed true lumen of the blood vessel. In particular, a radial support force in the preferred range is particularly conducive to a lesion site which has been formed for a certain period of time, where the torn vessel intima becomes hard and thus requires a greater force to be expanded.

Therefore, in an actual application, when the stent in the disclosure is released in the blood vessel (especially the aorta), the stent has different compression ratios along the axial direction thereof. The radial support forces at different sites of the stent may vary in a range of 100-1000 N, and the metal coverage at different sites of the stent may vary in a range of 30%-100%.

The stent in the disclosure needs to have a suitable weaving density. If weaving is too dense, radial compression may be difficult even by reducing the number of second wires. On the contrary, if weaving is too sparse, it is difficult to form effective obstructing on the tearing site of the intima even by axial compression.

Therefore, in an actual application, when the stent in the disclosure is released in the blood vessel (especially the aorta), the metal coverage at different sites of the stent may be different depending on different compression/stretching ratios, for example, the metal coverage may vary between a metal coverage at axial maximum compression and a metal coverage in the natural release state or in an appropriate stretching state.

Due to the above characteristics of the stent in the disclosure, it is possible to be relatively flexibly adapted to different treatment requirements, for example, from the ascending aorta to the abdominal aorta, for example meeting requirements of repairing the tear and maintaining smooth blood flow in the branch artery simultaneously.

According to an embodiment, in the natural release state, the stent has a substantially complete liquid permeability, that is, the blood flow from the aorta to the branch artery is substantially or completely not obstructed. According to this embodiment, in the natural release state, the stent has a metal coverage of 30%-60% and a radial support force of 200-600 N. The stent having a radial support force and a metal coverage in above specified ranges has a relatively low radial support force and a relatively low metal coverage in the natural release state, but has a relatively large compressible ratio. The stent may still create necessary radial support force and metal coverage, which meet the above provisions, after it is compressed, so as to effectively obstruct the tear of the inner wall of the blood vessel. In the release and axial maximum compression state, the stent has a metal coverage of 80-90%, and a radial support force of 400-1000 N.

According to another specific embodiment, in the natural release state, the stent has a metal coverage of 60%-90%, preferably a metal coverage of 70%-90%, and a radial support force of 100-600 N. The stent having a radial support force and a metal coverage in above specified ranges has a relatively high radial support force and a relatively high metal coverage in the natural release state, but has a relatively large extendable ratio. The stent may still be radially compressed to a suitable dimension after it is extended, so as to be assembled into a suitable delivery system. The stent in the embodiment has a relatively large radial support force and a relatively large metal coverage without compression after it is partially released, thereby facilitating immediate support and expansion of the true lumen of the blood vessel, and obstructing a tear to a certain extent. Further, the radial support force may be further enhanced and the metal coverage may be increased by axially compressing a local segment of the stent, so as to create the necessary radial support force and metal coverage, which meet the above provisions, thereby obstructing the tear of the inner wall of the blood vessel more effectively. In the release and axial maximum compression state, the stent has a metal coverage of 90%-100%, preferably a metal coverage of 90%-95%, and a radial support force of 500-1000 N.

According to this embodiment, in the natural release state, the stent has certain (rather than complete) liquid permeability, that is, the stent forms a certain obstruction of blood flow from the artery to the branch artery. In a specific embodiment, since the stent according to the disclosure is axially extendable, suitable blood permeability may be obtained by properly stretching a local segment of the stent corresponding to the branch vessel when the stent is placed. To this end, a corresponding portion of the stent is configured to have an increased diameter relative to an adjacent portion thereof, so that a diameter of this area after it is stretched is suitable for an inner diameter of a lumen, which has a branch vessel, of the blood vessel. In another specific embodiment, the stent is provided with at least one sparse mesh area. The sparse mesh area is formed only of the second wires by removing the first wires, and is arranged at branch arteries of a corresponding treatment site after the stent is released. That is, in this embodiment, except for the sparse mesh area, the stent in the disclosure is formed by weaving at least first wires and second wires, each of the first wires and each of the second wires having different diameters. The sparse mesh area is formed by weaving only the thicker second wires.

In this embodiment, the sparse mesh area includes at least a first sparse mesh area or a second sparse mesh area. The first sparse mesh area corresponds to an aortic arch site, and a central angle corresponding to the first sparse mesh area ranges from 120° to 180°. The second sparse mesh area corresponds to a branch artery site in an abdominal aorta, and a central angle corresponding to the second sparse mesh area is 180°. The branch arteries in the abdominal aorta are a left renal artery, a right renal artery, a coeliac trunk and a superior mesenteric artery, which are located on the abdominal aorta.

According to one solution, the treatment site includes the aortic arch. The sparse mesh area includes a first sparse mesh area corresponding to the greater curvature of the aortic arch, especially to the branch arteries on the aortic arch: a brachiocephalic trunk, a left common carotid artery, and a left subclavian artery. Specifically, a length of the first sparse mesh area is greater than a length of the branch artery area on the aortic arch, such as 6-8 cm, and a radian of the first sparse mesh area occupies about ⅓-½ circumference of this segment of the stent, that is, a central angle corresponding to the first sparse mesh area ranges from about 120° to about 180°. According to another solution, the treatment site includes the abdominal aorta. The sparse mesh area includes a second sparse mesh area corresponding to a branch artery site in the abdominal aorta, especially to the branch arteries on the abdominal aorta: a left renal artery, a right renal artery, a coeliac trunk and a superior mesenteric artery. Specifically, a length of the second sparse mesh area is greater than a length of a distribution area of the above-mentioned branch arteries on the abdominal aorta, such as 2-4 cm, and a radian of the second sparse mesh area occupies about ½ circumference of this segment of the stent, that is, a central angle corresponding to the second sparse mesh area is about 180°. In different solutions, the stent may be provided with the first and second sparse mesh areas.

In this embodiment, any one of the apertures of the sparse mesh area is expandable, allowing a branch stent to be placed through the expanded aperture.

The stent according to this embodiment may be woven according to the metal coverage requirements for other portions of the stent. After weaving is completed, the first wires are removed in an area where the sparse mesh area is intended to be formed, thereby forming the sparse mesh area.

According to yet another embodiment, the stent in the disclosure is used in the aorta including an area of an abdominal aorta, and the stent is internally provided with two common iliac artery stent fixing parts, which are configured to fix a left common iliac artery stent and a right common iliac artery stent.

Specifically, the two common iliac artery stent fixing parts are arranged inside the stent and correspond to the abdominal aorta close to a bifurcation of left and right common iliac arteries, and the two common iliac artery stent fixing parts are configured as two annuluses tangent to each other and are integrally formed with an inner wall of the stent.

Unlike a fixing part forming two cylindrical branches at a lower portion of a stent for the abdominal aorta, the two fixing parts of the stent in the disclosure are arranged inside the stent, so that the exterior of the stent remains to be cylindrical, which is more conducive to expanding the blood vessel, without becoming less supportive in the vicinity of the common iliac arteries. Furthermore, the common iliac artery fixing parts are integrally formed with the stent, so that the left common iliac artery stent and the right common iliac artery stent may be fixed more stably.

According to a preferred embodiment, the first wire for the stent in the disclosure may have a diameter of 50-150 μm, and the second wire may have a diameter of 150-600 μm. The stent is formed by weaving 48-202 wires, among which 4-32 wires are the second wires, and remaining wires are the first wires.

According to an embodiment, the stent is formed by weaving three kinds of wires with different diameters. The second wires may include first thick wires and second thick wires, each of the first thick wires and each of the second thick wires having different diameters. According to a specific embodiment, the first thick wire may have a diameter of 150-300 μm, and the second thick wire may have a diameter of 300-600 μm. The stent may be formed by weaving 48-202 wires, among which the second wires include 6-24 first thick wires and 4-24 second thick wires, and remaining wires are the first wires, provided that a sum of a number of the first thick wires and a number of the second thick wires is less than or equal to 30.

According to another embodiment, the stent is formed by weaving three kinds of wires with different diameters. The first wires may include first thin wires and second thin wires, each of the first thin wires and each of the second thin wires having different diameters. According to a specific embodiment, the first thin wire may have a diameter of 50-100 μm, and the second thin wire may have a diameter of 100-150 μm. The stent is formed by weaving 48-202 wires, among which 4-30 wires are the second wires, and remaining wires are the first wires. The first wires include 32-198 first thin wires and 32-198 second thin wires, provided that a sum of a number of the first thin wires and a number of the second thin wires is less than or equal to 198.

According to yet another embodiment, the stent is formed by weaving four kinds of wires with different diameters, i.e., the first and second thin wires as well as the first and second thick wires as described above.

If the number of thick wires (i.e., second wires) is excessive, the stent cannot be effectively compressed to the desired delivery state. However, if the number of thick wires is too small, the stent cannot provide the expected radial support force even after being compressed, and the expected structure and morphology of the stent cannot be maintained in the release state. Furthermore, the thin wires (i.e., the first wires) fill the gaps between the second wires, and may increase the metal coverage without excessively increasing the support force, thereby effectively obstructing the tear in the blood vessel. However, the amount of first wires should not be too much. If the amount of the first wires is too much, it is still difficult to compress the stent to a delivery state with a suitable diameter.

According to an embodiment of the disclosure in which the stent has a metal coverage of 30%-60% and a radial support force of 200-600 N in the natural release state, the number of wires for weaving the stent may be 48-156, preferably 48-128. The number of second wires may be 4-30, and the remaining wires are the first wires. According to a specific embodiment, the stent is formed by weaving two kinds of first wires and one kind of second wire. 4-30 of second wires may be used, and the remaining wires are the first wires. The first wires may include 32-120 first thin wires and 32-120 second thin wires, provided that a sum of a number of the first thin wires and a number of the second thin wires does not exceed 152. According to another specific embodiment, the stent is formed by weaving one kind of first wire and two kinds of second wires. The second wires include 6-24 first thick wires and 6-24 second thick wires, and the remaining wires are the first wires, provided that a sum of a number of the first thick wires and a number of the second thick wires does not exceed 30.

According to an embodiment of the disclosure in which the stent has a metal coverage of 60%-90% and a radial support force of 100-600 N in the natural release state, the number of wires for weaving the stent may be 96-202, preferably 96-156. The number of second wires may be 4-30, preferably 4-24, and the remaining wires are the first wires. According to a specific embodiment, when the thick wires including two different diameters are used, the second wires may include 6-12 first thick wires and 4-12 second thick wires, and the remaining wires are the first wires. If the number of thick wires (i.e., second wires) is excessive, the stent cannot be effectively compressed to the desired delivery state. However, if the number of thick wires is too small, the stent cannot provide the expected radial support force even after being compressed, and the expected structure and morphology of the stent cannot be maintained in the release state. According to yet another specific embodiment, when the thin wires with two different diameters are used, 4-30 wires, preferably 4-24 wires are the second wires, and the remaining wires are the first wires. The first wires include 32-120 first thin wires and 32-120 second thin wires, provided that a sum of a number of the first thin wires and a number of the second thin wires does not exceed 198.

According to an embodiment, the stent is formed of at least two layers of woven meshes. According to an embodiment, the stent is provided with two to four layers of woven meshes. In a case that the stent is provided with multiple layers of woven meshes, the stent has the radial support force and the metal coverage as specified above as a whole.

A method for weaving the stent in the disclosure is not specifically limited. A conventional overlapping and weaving method may be used (that is, there is no constraint at an intersection between the wires), as long as it may facilitate the axial compression and stretching of the stent.

It should be understood that according to a radial support force range and a metal coverage range required by a specific treatment type, those skilled in the art may select a suitable woven material and determine a reasonable number of layers under specific equipment conditions according to the descriptions herein, further select a suitable diameter, number, or the like of the wires, and determine a suitable weaving solution to obtain a stent having the desired radial support force range and metal coverage range. For example, the suitable weaving solution may be designed by dedicated software.

According to a further embodiment, a tip of the stent in the disclosure (especially a proximal end, at which the stent has a maximum radial support force) may be formed in a return weaving manner. As for the other tip of the stent, if there is a burr which cannot be woven in a return weaving manner again, the burr may be positioned on an inner side of the stent by selecting a suitable arrangement of each layer. Alternatively, if there are two layers of burrs, one of the two layers of burrs is woven in a return weaving manner by a small distance, so as to wrap the other one of the two layers of burrs in the segment which is woven in a return weaving manner. Alternatively, if multiple stents are used in conjunction with each other, a single layer of burr or two layers of burrs may be overlapped in another dense mesh stent. The stent according to this embodiment is provided with a smooth tip, thereby avoiding mechanical damage to the inner wall of the blood vessel by the exposed wire tip (burr).

According to the disclosure, the stent has the same diameter as a whole, or the stent has a variable diameter, and the diameter of the stent ranges from 20 cm to 55 cm.

According to an embodiment, in the release state, the stent in the disclosure is provided with a first segment at the proximal end of the stent. The first segment may have a diameter of 35-55 mm, so as to be suitable for the ascending aorta. A length of the first segment ranges from 8 cm to 11 cm, preferably from 8 cm to 10 cm. The stent may be further provided with a second segment adjacent to the first segment. The second segment may have a diameter of 20-38 mm, so as to be suitable for a portion in the artery from the aortic arch to the abdominal aorta. The second segment extends from the first segment to a distal end of the stent. A length of the second segment may range from 28 cm to 40 cm, preferably from 28 cm to 31 cm.

According to another embodiment, the stent may have a diameter of 20-38 mm, so as to be suitable for a part of the abdominal aorta. In this embodiment, the stent may have a length of 28-40 cm, preferably 28-31 cm.

The stent in the disclosure is self-expandable or capsule-expandable. Materials of the first wires and the second wires for weaving the stent may be different, but preferably the same. Generally, the material of the wire may be metal, such as a shape memory alloy (e.g., Nitinol), cobalt-chromium alloy, tungsten, or tantalum.

A second aspect of the disclosure provides a stent kit. The stent kit is used in an aorta, especially used in an area from an ascending aorta to an abdominal aorta. The stent kit includes a first stent used in an area from the ascending aorta to an aortic arch, a second stent used in an area of a descending aorta, and a third stent used in an area of the abdominal aorta. Each of the first stent, the second stent and the third stent may be the stent in the disclosure as defined above.

In particular, the first stent has a diameter of 38-55 mm, and a length of 8-11 cm, preferably a length of 8-10 cm, the second stent has a diameter of 25-35 mm and a length of 15-20 cm, and/or the third stent has a diameter of 20-30 mm and a length of 15-20 cm.

The stent kit in the disclosure may be combined more flexibly directing to the requirements of different areas of the blood vessel, and each stent may have different lengths, diameters, radial support forces and metal coverage. Furthermore, operation of a shorter stent is more flexible. The stent kit provides a complete and flexible solution for lesion in the entire area from the ascending aorta to the abdominal aorta.

According to an embodiment, a distal end of the first stent may be inserted inside a proximal end of the second stent, and a distal end of the second stent may be inserted inside a proximal end of the third stent, so that the three stents are connected end-to-end, thereby providing a gapless and uniform support for the aorta. In this embodiment, the distal ends of the first stent and the second stent may have burrs. The burrs are respectively received inside the proximal ends of the second stent and the third stent, thereby avoiding possible damage to the vascular tissues and reducing the thickness of the stents. Meanwhile, tips of the stents in direct contact with the inner wall of the blood vessel are formed as smooth tips in a return weaving manner.

A third aspect of the disclosure provides a stent delivery system, including a delivery catheter and the stent according to the disclosure as defined above.

The delivery catheter includes an outer catheter, an inner catheter and a push rod, in which the outer catheter, the inner catheter and the push rod are arranged coaxially with one another and arranged sequentially from exterior to interior of the delivery catheter.

The outer catheter is provided with a proximal end portion and a distal end portion, and the other catheter is provided with a first hollow cavity penetrating through the outer catheter.

The inner catheter extends in the first hollow cavity at the distal end portion of the outer catheter, and the inner catheter is provided with a second hollow cavity penetrating through the inner catheter.

The push rod extends through the first hollow cavity of the outer catheter and the second hollow cavity of the inner catheter, and extends out of a distal end of the inner catheter.

The stent is releasably maintained between the push rod and the outer catheter in a delivery configuration and is arranged in the first hollow cavity at the proximal end portion of the outer catheter.

The delivery catheter is configured so that the outer catheter, the inner catheter and the push rod are axially movable relative to one another, and one end of the stent is removably constrained to a proximal end of the push rod, and another end of the stent is removably constrained to a proximal end of the inner catheter.

According to an embodiment, in the stent delivery system in the disclosure, both ends (i.e., the proximal end and the distal end) of the stent in the disclosure are removably constrained to the proximal end of the push rod and the proximal end of the inner catheter, respectively. In this way, when the stent is released, the outer catheter is maintained stationary and the push rod is pushed in a direction toward the heart, so that the push rod may drive the stent and the inner catheter to move in the direction toward the heart, while the outer catheter correspondingly moves in a direction away from the heart, so that the stent starts to be released from the proximal end of the stent.

Since the proximal end of the stent is constrained to the proximal end of the push rod, the stent is not fully expanded and is in a semi-release state during initial release. At this time, a diameter of the stent has not reached a diameter in a full-release state of the stent, so that the stent does not abut against the vessel wall, allowing the position of the stent to be easily adjusted. Furthermore, for example, the partially released stent may be withdrawn into the delivery catheter, and may be released again after its position is adjusted. Constraint of the proximal end of the stent to the proximal end of the push rod also has another benefit, that is, a frictional resistance between the stent and the outer catheter is reduced during initial release, since the end of the stent is constrained. Reduction of the frictional resistance is very advantageous for release of the stent, especially for release of the stent in the ascending aorta. Since the delivery catheter turns nearly 180° after passing through the aortic arch, a pushing direction of the push rod at the operator side is almost opposite to a movement direction of the push rod at the ascending aorta side. Therefore, the lower the friction between the stent and the outer catheter, the smaller the force used by the operator to push the push rod, and the easier for the operator to control the release process, thereby facilitating the stable release of the stent.

When at least a portion of the stent is released, one end of the stent is maintained stationary, and the other end of the stent is moved toward said one end (for example, the inner catheter and the outer catheter are maintained stationary, and the push rod is pulled back), so that the released portion of the stent may be compressed, thereby obstructing the tear and supporting the true lumen of the blood vessel as described above.

Methods for constraining both ends of the stent are not specifically limited, and any existing constraining methods which be removed finally may be used. For example, both ends of the stent may be temporarily fixed to the push rod and the inner catheter by conventional stoppers, respectively.

The stent delivery system in the disclosure may have a conventional outer diameter, thereby facilitating placing, through the femoral artery, the stent at a site in the aorta that needs to be treated. According to the disclosure, even a stent to be released in the ascending aorta, this stent may also be assembled in the delivery catheter by axially extending and radially compressing this stent to a suitable diameter.

According to an embodiment, an outer diameter of the outer catheter of the stent delivery system in the disclosure ranges from about 5 mm to about 10 mm, preferably from about 5 mm to about 7 mm.

According to an embodiment, the push rod is hollow for passage of the guide wires.

According to a fourth aspect of the disclosure, a stent placement method is further provided, which includes the following operations.

The stent delivery system according to the disclosure is guided to a treatment site.

At least a portion of the stent according to the disclosure is released.

One end of the released portion of the stent is maintained stationary, and the stent delivery system is manipulated, so that the other end of the released portion of the stent moves along an axial direction of the stent to compress/extend the released portion.

After the stent is completely released, constraints on both ends of the stent are removed.

According to the stent placement method, position of the stent is adjusted after the stent is released for a certain length, and the push rod may be pulled back in a direction away from the heart when positions of the inner catheter and the outer catheter are fixed and remained unchanged for example (or, the inner catheter and the outer catheter may be pushed in a direction toward the heart when position of the push rod is fixed and remained unchanged), so that the semi-released stent is driven to be axially compressed. Such axial compression is achieved due to the fact that in the stent delivery system in the disclosure, both ends of the stent are constrained, or a portion of the stent has been released and fixed by abutting against the vessel wall, so that when one end is fixed and the other end is moved, the released portion of the stent may be axially compressed/stretched. For a site where a tear of the blood vessel is located, with the stent delivery system in the disclosure, the released segment of the stent may be compressed to its maximum or appropriate metal coverage and its maximum or appropriate radial support force, so that the released segment tightly abuts against the vessel wall at a corresponding site (especially a tearing site of the intima) under the action of its radial support force, thereby completing the release of this segment.

Similarly, other portions of the stent may be selected to be completely released directly as desired, or may be simultaneously released and compressed/stretched in different segments. After the final release substantially completes, constraints on both ends of the stent are removed, and the delivery catheter is withdrawn from the lumen of the blood vessel together with the push rod.

The stent placement method in the disclosure further includes the following operations. It is detected whether a release position is correct after at least the portion of the stent according to the disclosure is released.

When it is found that the release position is incorrect, the stent delivery system is adjusted so that the released portion is located at a correct position; or the released portion is withdrawn into the delivery catheter, the stent delivery system is adjusted to a correct position, and the stent is released again.

Since in the stent delivery system in the disclosure, both ends of the stent are temporarily constrained, the stent may be compressed or stretched in different segments during release of the stent. In particular, for the tearing site of the inner wall of the blood vessel, effective obstructing and a desired radial support force may be created at this local area by compression operations, so as to achieve the best therapeutic effect. Meanwhile, other portions or specific portions of the stent do not obstruct the blood flow, so that there is no risk caused by interruption or deficiency of blood supply to the branch artery.

Optionally, according to an embodiment, in the branch artery area, a larger aperture may also be formed at this local area by stretching operations, so as to facilitate placement of the branch stent in the branch vessel. According to another embodiment, since the stent in the disclosure is formed by the overlapping and weaving method, any one of the apertures is expandable, the branch stent may also be placed directly through the expanded aperture. According to still another embodiment, the stent provided with the above-mentioned sparse mesh area in the disclosure may be used, so as to facilitate placement of the branch stent.

According to an embodiment, in this method, the operation that at least the portion of the stent is released includes the following operation. The stent starts to be released from the proximal end of the stent.

According to an embodiment, in this method, compressing the released portion of the stent is performed by compressing the proximal end of the stent. Since a tear of the aortic dissection usually occurs at an end of the dissection close to the heart, the proximal end of the stent is usually required to be compressed, so as to obstruct the tear. According to the method in the disclosure, the delivery catheter is withdrawn from the treatment site after the placement of the stent is completed.

According to an embodiment, the method further includes the following operations. The stent delivery system is introduced from a subject's femoral artery, and the delivery catheter is withdrawn after the stent is placed.

According to an embodiment, the method further includes the following operation. The stent delivery system is guided to the treatment site by the guide wires.

According to an embodiment, the subject is a mammal, preferably a pig or a human, more preferably a human, most preferably a yellow race.

According to an embodiment, the treatment site is any site from the ascending aorta to the abdominal aorta. According to a specific embodiment, the treatment site includes a tearing site of the vessel intima. According to a more specific embodiment, the treatment site further includes a branch vessel.

According to a fifth aspect of the disclosure, a method for treating a subject's aortic dissection or aortic aneurysm is further provided, which includes the following operations. The stent in the disclosure is placed in a treatment site in the aorta of the subject to be treated according to the above stent placement method.

DETAILED DESCRIPTION

Figure 1:
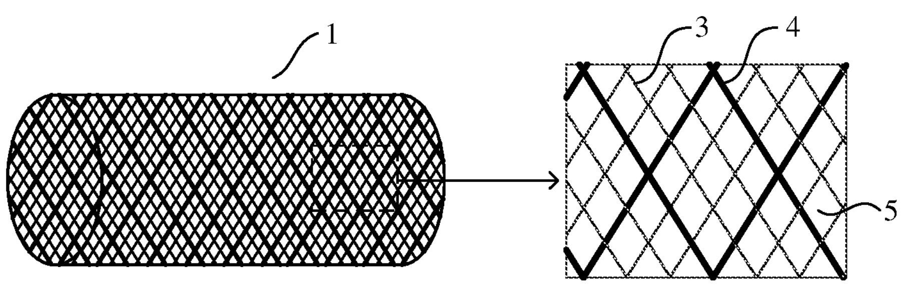
FIG. 1 is a schematic view and partially enlarged view of a stent according to an embodiment of the disclosure.

Technical solutions in embodiments of the disclosure will be clearly and completely described below in combination with the embodiments of the disclosure and the accompanying drawings. It is apparent that the described embodiments are only part of the embodiments of the disclosure, rather than all the embodiments, and the technical solutions recited in the embodiments of the disclosure may be implemented in any combination without conflict. All other embodiments obtained by those of ordinary skill in the art based on the embodiments of the disclosure without any creative efforts belong to the protection scope of the disclosure.

Throughout the description, terms used herein should be understood as meanings as usually used in the art, unless specifically stated otherwise. Therefore, unless defined otherwise, all technical and scientific terms used herein have same meanings as usually understood by those skilled in the art to which the disclosure belongs. When there is a contradiction, meanings of the description are preferred.

Like reference numerals in the accompanying drawings refer to like components. Shapes and dimensions of components in schematic drawings are for illustration only and cannot be considered to reflect actual shapes, dimensions and absolute positions.

It should be noted that in the disclosure, terms “including”, “include”, or any other variants thereof are intended to cover a non-exclusive inclusion, so that a method or device including a series of elements not only includes elements which are explicitly recited, but also includes other elements which are not explicitly listed, or further includes elements inherent to implementation of the method or device.

It should be noted that terms “first\second” involved in the embodiments of the disclosure are only intended to distinguish similar objects, and do not represent a specific sequence of the objects, and it may be understood that “first\second” may exchange a specific sequence or order in an allowable situation. It should be understood that objects distinguished by “first\second” may be interchanged in an appropriate situation, to enable embodiments and examples of the disclosure described here to be implemented in an order other than those illustrated or described herein.

In order to describe the disclosure more clearly, terms “proximal end” and “distal end” are customary terms used in the field of intervention medical treatment. Herein, “distal end” indicates an end away from the heart during operation, and “proximal end” indicates an end close to the heart during operation.

Stent

The disclosure provides a stent used in an aorta. The stent is formed by weaving wires with at least two different kinds of diameters, and is configured to be at least partially compressible and extendable along an axial direction of the stent in a release state.

FIG. 1 shows a schematic view and partially enlarged view of a stent 1 according to the disclosure. The stent 1 is formed by overlapping and weaving multiple first wires 3 and multiple second wires 4. Therefore, the stent in the disclosure is a bare stent. The stent 1 shown in FIG. 1 is a single-layer mesh structure provided with apertures 5.

The stent in the disclosure may also have a structure with multiple layers, such as 2-4 layers. For example, the multiple layers may be formed in a return weaving manner.

The stent in the disclosure is suitable for any segment from the ascending aorta to the abdominal aorta or the whole aorta, and thus may have a diameter from about 55 mm to about 20 mm.

According to the disclosure, the stent 1 may be formed by weaving a total of 48-202 wires. For example, as may be enumerated, the stent in the disclosure may be formed by weaving 48, 64, 96, 128, 156, 196 wires or the like. The number of wires may be determined according to the diameter of the stent, the number of layers, the materials of the used wires, or the like.

The material of the stent in the disclosure may be any material suitable for a peripheral vascular stent, as long as the material may provide a sufficient radial support force and have certain fineness. Generally, metal wires such as nickel-titanium alloy wires, cobalt-chromium alloy wires, tungsten wires, tantalum wires, or the like are preferably used, more preferably the nickel-titanium alloy wires.

There are at least four second wires 4 used as thick wires. However, the number of second wires is no more than 32, generally, no more than 30. A diameter of the second wire 4 is comprised between 150 μm and 800 μm, preferably between 150 μm and 600 μm, such as 150 μm, 200 μm, 250 μm, 300 μm, 350 μm, 400 μm, 450 μm, 500 μm, 550 μm, or 600 μm. The second wire 4 provides a basic support force and a complete structure for the stent 1. However, the number of second wires cannot be too much. For example, even though only wires with the diameter of 300 μm are used, when there are about 32 wires, it is difficult to compress the stent, especially for a stent portion with ultra-large diameter greater than about 40 mm, to a suitable delivery dimension, so that the stent cannot be used.

In the stent 1, except for the thick wires, the remaining wires are the first wires 3 used as thin wires. A diameter of the first wire 3 in the disclosure may range from 20 μm to 150 μm, preferably from 50 μm to 150 μm, such as 30 μm, 40 μm, 50 μm, 60 μm, 70 μm, 80 μm, 90 μm, 100 μm, 110 μm, 1120 μm, 130 μm, 140 μm and 150 μm. The first wires 3 provide the functions of auxiliary supporting the stent 1 and filling the gaps between the second wires 4. Furthermore, since the number of first wires 3 is much greater than that of second wires 4, the first wires 3 also provide a function of maintaining the shape of the stent 1. The inventors have found that although it seems to be feasible theoretically, in fact, with the overlapping and weaving method in the disclosure, a large-diameter stent with a certain shape and a sufficient support force cannot be formed by the second wires (i.e., the thick wires) alone. Furthermore, a large-diameter stent with a fixed wire-to-wire intersection formed by using for example a laser engraving technology, has a much smaller support force, even though the diameter of the wires is the same, which cannot meet the requirements for use in the aortic vessel in the disclosure.

The stent 1 in the disclosure is formed by weaving in an overlapping manner, and an ordered relative movement may happen at an intersection between the wires, so that any aperture 5 on the stent 1 in the disclosure may be easily expanded or compressed.

Figure 2:
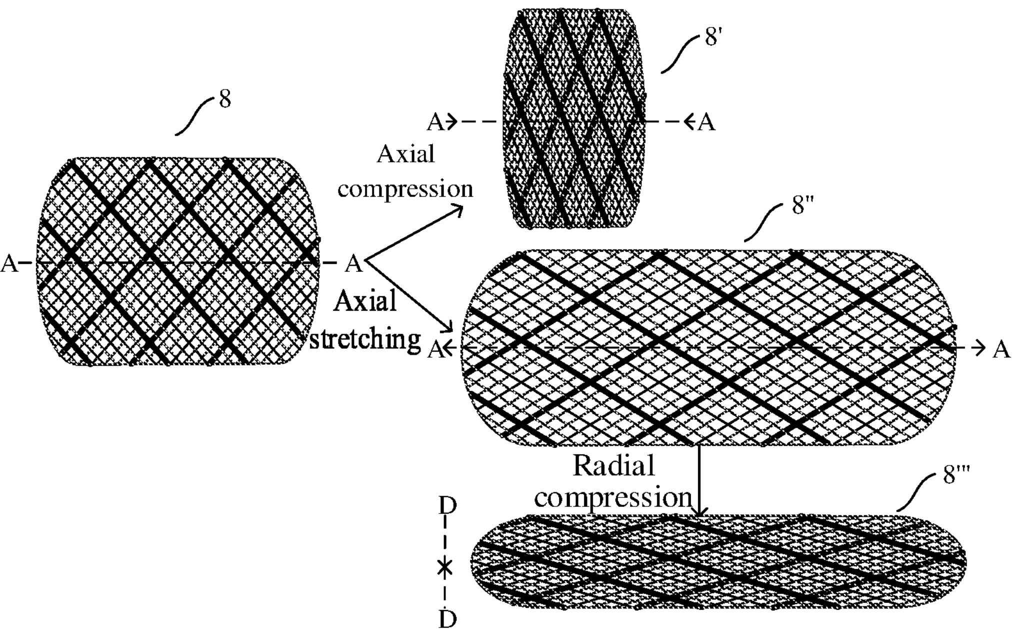
FIG. 2 is a schematic view of partially axial compression, axial stretching and further radial compression of the stent according to the disclosure.

With reference to FIG. 2, one end of a stent 8 in the disclosure is fixed, and the other end of the stent moves along an axial direction A-A, so that the stent may be axially compressed 8' or stretched 8".

The “axial direction” of the stent as mentioned herein refers to a direction along A-A as shown in FIG. 2, which is a direction of a central axis of a cylindrical shape of the stent. The "radial direction" of the stent as mentioned herein refers to a direction along D-D as shown in FIG. 2, which is a direction of any diameter of a circle of the cylindrical shape of the stent. In general, "radially compressed" herein refers to compression in a direction from the circumference to the center of the circle.

The above characteristics of the stent in the disclosure may provide many benefits. With reference to FIG. 2, since the stent 8 may be axially stretched, the density of woven wires, especially the second wires, is significantly reduced per unit length. Therefore, the stent 8" after being properly stretched is easily compressed radially to a stent 8''' with a smaller diameter, so as to be assembled into a delivery system with a conventional outer diameter (e.g., 5-10 cm, preferably 5-7 cm). Therefore, if necessary, such method may be used to solve the following problems in the related art: a stent with a large dimension and a high support force cannot be assembled into a delivery system with a suitable diameter. Furthermore, since the stent may be axially compressed, the compressed stent creates a high metal coverage, and the density of the second wires per unit length is increased to obtain a high radial support force. The high radial support force may achieve effective expansion of a narrowed part of the blood vessel, and the high metal coverage may achieve very low fluid permeability, thereby effectively obstructing the tear of the vessel intima. In this case, the second wires 4 in the stents 1, 8 act as a support skeleton, and the first wires 3 fill the gaps between the second wires 4 to act as a fabric membrane similar to the covered stent. Unlike the covered stent, the stent in the disclosure may provide a relatively high radial support force after being axially compressed, and the stent may even be effectively used for the treatment of type A aortic dissection involving the ascending aorta. Therefore, the stent in the disclosure also solves following problems in the related art: a conventional dense mesh stent or covered stent is difficult to be applied into the ascending aorta.

In a natural release state, a radial support force of the stent 1 in the disclosure may be no less than 100 N, preferably from 100 N to 600 N. In an axial maximum compression state, a radial support force of the stent 1 in the disclosure may be no less than 400 N, preferably from 400 N to 1000 N.

The "natural release state" of the stent as mentioned herein refers to a state in which the stent is not axially compressed and released, when it is fixed in a water bath at 37±2° C.

The "axial maximum compression state" of the stent as mentioned herein refers to a state in which the stent is axially compressed until it is unable to be further compressed, when it is in the natural release state.

The "radial support force" of the stent as mentioned herein refers to a force required to compress the stent along a diameter direction to reach 85% of its original diameter, after it is fixed in the natural release state.

Along with the radial support force, the stent in the disclosure also requires a high liquid impermeability to obtain an effect of effectively obstructing the tear of the vessel intima. This property may be represented by the metal coverage. In the natural release state, the stent 1 in the disclosure may have a metal coverage of 30%-90%. In the axial maximum compression state, the stent 1 in the disclosure may have a metal coverage of 80%-100%, preferably a metal coverage of 80%-95%.

The "metal coverage" of the stent as mentioned herein refers to a metal coverage ratio per unit area calculated by electron microscope scanning.

According to an embodiment, in the natural release state, the stent may have a radial support force no less than 200 N, and may have a metal coverage of 30%-60%. In this embodiment, the weaving density of the stent is relatively low, so that the radial support force of the stent is also relatively low in the natural release state. In this embodiment, the stent has a high axial compressible ratio, so that the desired radial support force and metal coverage may still be obtained after the stent is compressed. When the stent is placed, a relatively long segment of the stent needs to be released and then compressed, which requires the blood vessel to have a longer straight segment. Thus, the stent is not suitable for a site where a turn is present in the blood vessel, such as the ascending aorta.

According to another embodiment, in the natural release state, the stent may have a radial support force no less than 100 N, and may have a metal coverage of 60%-90%, preferably a metal coverage of 70%-90%. In this embodiment, the weaving density of the stent is relatively high, so that the radial support force of the stent is also relatively high in the natural release state. In this embodiment, the stent has a low axial compressible ratio, so that a certain radial support force and metal coverage may be obtained without compression after the stent is released. Thus, the stent is suitable to be placed in a site with a shorter straight segment in the blood vessel, such as the ascending aorta.

In this embodiment, when the stent is fixed in the blood vessel, the blood flow at the branch artery may also be adapted by stretching the stent.

Figure 3:
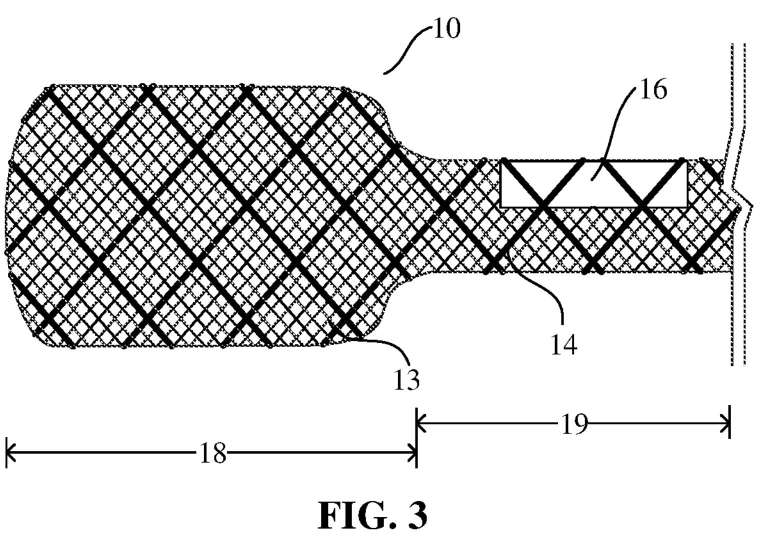
FIG. 3 is a schematic view of a stent according to another embodiment of the disclosure.

The stent in this embodiment has a relatively high metal coverage in the natural release state, so as to hinder the blood flow to a certain extent. In order to maintain smooth blood flow at the branch artery, the stent in this embodiment is provided with at least one sparse mesh area. With reference to FIG. 3, a single-layer structure of a stent 10 in this embodiment suitable to be placed at a site from the ascending aorta to the aortic arch is schematically shown. The stent 10 may be provided with multiple layers, such as 4 layers, so as to obtain a metal coverage in the above range. In order to clearly illustrate a specific structure of the stent, only a single layer is shown in FIG. 3. The stent 10 includes a segment 18 suitable for the ascending aorta and a segment 19 suitable for the aortic arch. A diameter of the segment 18 suitable for the ascending aorta ranges from about 38 mm to about 55 mm, and a diameter of the segment 19 suitable for the aortic arch is reduced to about 20 mm to about 35 mm. A sparse mesh area 16 is provided in the segment 19 suitable for the aortic arch. The sparse mesh area 16 is only provided with the second wires (i.e., the thick wires) 14. Portions other than the sparse mesh area 16 is further provided with the first wires (i.e., the thin wires) 13 besides the second wires. The sparse mesh area 16 is arranged at a site corresponding to a greater curvature of the aortic arch after the stent is released, and the sparse mesh area is provided with an area larger than an opening of the branch vessel of the greater curvature in the artery. Typically, the sparse mesh area 16 corresponding to the greater curvature may have a length of about 6-8 cm, and occupies about ⅓ to about ½ arc length of the circumference of the segment 19 of the stent 10.

Figure 4:
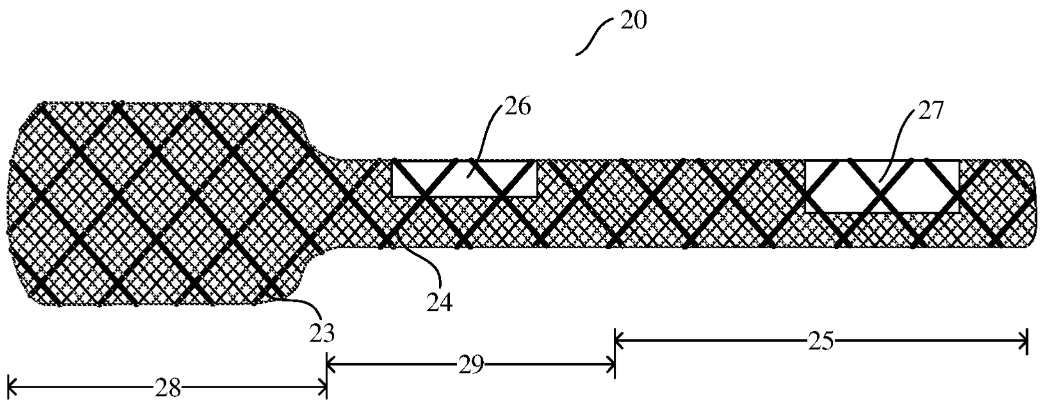
FIG. 4 is a schematic view of a stent according to yet another embodiment of the disclosure.

According to another example, as shown in FIG. 4, the stent 20 may be suitable for the entire arterial area from the ascending aorta to the abdominal aorta. FIG. 4 schematically shows a schematic view of a single layer of a stent 20 provided with two sparse mesh areas. Although FIG. 4 only shows a single layer, the stent 20 in this embodiment may be provided with 2-4 woven layers which are woven in the same manner.

As shown in FIG. 4, the stent 20 includes a segment 28 corresponding to the ascending aorta, a segment 29 corresponding to the aortic arch, and a segment 25 corresponding to an area from the descending aorta to the abdominal aorta. The segment 28 corresponding to the ascending aorta may have a diameter of 38-60 mm, such as 38-55 mm, and a length of 8-11 cm. The segment 29 corresponding to the aortic arch may have a diameter gradually reduced in a range of 20-45 mm, such as about 20-35 mm. The segment 25 corresponding to the area from the descending aorta to the abdominal aorta may extend from an area behind the aortic arch to an area of the abdominal aorta, and a diameter of the segment 25 may vary from about 25 mm-about 30 mm to about 20 mm-about 25 mm. The segment 29 corresponding to the aortic arch may have a length of 8-11 cm, and the segment 25 corresponding to the area from the descending aorta to the abdominal aorta may have a length of 20-40 cm for example, such as a length of 25-31 cm.

The stent 20 in this embodiment is also formed by interleaving the first wires 23 and the second wires 24.

The stent 20 may include two sparse mesh areas 26, 27 formed only of the second wires 24, i.e., a first sparse mesh area 26 corresponding to the branch arteries (a brachiocephalic trunk, a left common carotid artery, and a left subclavian artery) at the aortic arch, and a second sparse mesh area 27 corresponding to the branch arteries (a left renal artery, a right renal artery, a coeliac trunk, and a superior mesenteric artery) at the abdominal aorta. The first sparse mesh area may have a dimension in the embodiment as shown in FIG. 1. The second sparse mesh area may have a length of about 2-4 cm, and occupies about ½ arc length of the circumference of this segment.

The stent shown in FIG. 1 and FIG. 3 may be formed by weaving in a conventional manner, and then the first wires 13, 23 in predetermined areas are removed to form the sparse mesh areas 16, 26, 27.

Figure 5:
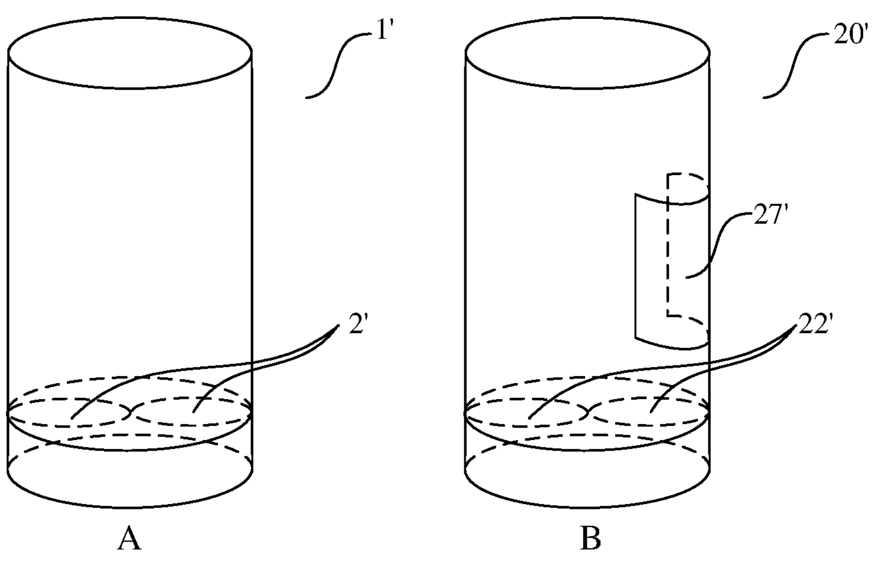
FIG. 5 shows schematic partial views of variations of a stent (A) according to the embodiment shown in FIG. 1 and a stent (B) according to the embodiment shown in FIG. 3.

According to a further embodiment, at a corresponding treatment site which is the abdominal aorta, the stent in the disclosure may be provided with two common iliac artery stent fixing parts, which are configured to receive and fix a left common iliac artery stent and a right common iliac artery stent. With reference to FIG. 5, a stent 1'(A) without a sparse mesh area and a stent 20'(B) with a sparse mesh area 27' in this embodiment are schematically shown. The stents 1', 20' shown in FIG. 5 are suitable for a segment of the abdominal aorta and is provided with the sparse mesh area 27'. The two common iliac artery stent fixing parts 2', 22' configured as two adjacent annular channels are provided inside the stents 1', 20' at the lower portions of the stents 1', 20'. For the sake of clarity, each of the fixing parts 2', 22' is shown as a plane in FIG. 5. In fact, each of the fixing parts 2', 22' has a certain thickness. In some examples, the common iliac artery stent fixing parts 2', 22' may extend downward to the distal ends of the stents 1', 20' respectively.

Each of the common iliac artery stent fixing parts 2', 22' is also formed by weaving the same first and second wires as the stents 1, 20 (the first and second wires are not shown), and is integrally formed with the stent. The exteriors of the two annuluses are integrally woven with an inner wall of the stent. The inner diameters of the two annuluses are adapted to the outer diameters of the left and right common iliac artery stents to be received and fixed, usually slightly smaller than the outer diameters of the left and right common iliac artery stents, so as to fix the common iliac artery stents.

Figure 6:
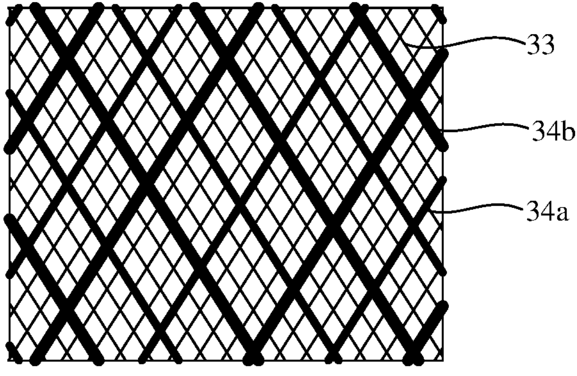
FIG. 6 is a schematic partially enlarged view of a stent according to an embodiment of the disclosure.

According to an embodiment, the stent in the disclosure may be formed by weaving three or more wires with different diameters. As shown in FIG. 6, a schematic partially enlarged view of a single layer of the stent in this embodiment is shown. The stent is formed by weaving one kind of first wire 33 and two kinds of second wires 34*a*, 34*b*. The first wires 33 are thin wires, which may have a diameter of 20-150 μm, preferably a diameter of 50-150 μm. The second wires include first thick wires 34*a* which may have a diameter of 150-300 μm, and second thick wires 34*b* which may have a diameter of 300-600 μm. 6-12 first thick wires may be used, more than 4 but no more than 12 second thick wires may be used, and the remaining wires are the first wires. This embodiment may also have other variations, for example, the stent is formed of two kinds of first wires (for example, their diameters are in a range of 20-100 μm and a range of 100-150 μm, respectively) and one kind of second wire, or formed of two kinds of first wires and two kinds of second wires, which is not limited thereto.

A radial support force of the stent formed of three or more kinds of wires with different diameters is more uniform throughout the stent, and the flexibility of the stent may also be enhanced.

Figure 7:
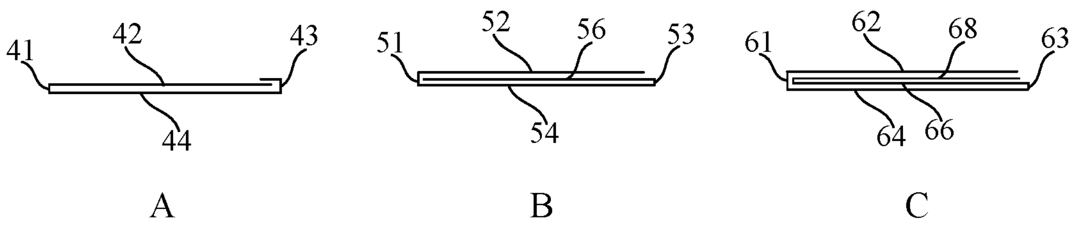
FIG. 7 is a schematic cross-sectional view of a multi-layer stent wall according to the disclosure.

As described above, the stent in the disclosure may be provided with multiple layers, preferably two layers, three layers, or four layers. According to a preferred embodiment, the multi-layer stent may be formed by return weaving a single-layer woven mesh. As shown in A to C in FIG. 7, schematic cross-sectional views of walls of stents with two to four layers are shown. A in FIG. 7 shows a two-layer structure. An upper layer 42 of the structure in this figure is located at a side of the stent close to interior, and a lower layer 44 is located at a side of the stent close to exterior (i.e., a side in contact with the vessel wall). In this structure, a smooth tip is formed at a proximal end 41 in a return weaving manner. At a distal end 43, the lower layer 44 facing toward the exterior of the stent is woven in a return weaving manner by a certain distance, so as to wrap an opened edge (burr) at a distal end of the upper layer 42 facing toward the interior of the stent, inside the lower layer 44, thereby forming two smooth tips at both ends. Similarly, in B in FIG. 7, an upper layer 52 is woven in a return weaving manner at a proximal end 51 to form a lower layer 54, and the upper layer 52 is further woven in a return weaving manner at a distal end 53 to form an intermediate layer 56. At the distal end 53, the lower layer 54 and the intermediate layer 56 are slightly longer than the upper layer 52, so that an opened edge at the distal end of the upper layer is located inside the stent. In this way, both ends of the stent are also smooth tips. The same principle is also applied to four layers in C in FIG. 7. At a distal end 63, two layers 62, 68 close to the interior of the stent are shorter than an edge formed by return weaving two layers 64, 66 close to the exterior of the stent, while at a proximal end 61, a lowermost layer 64 is formed by return weaving an uppermost layer 62, so as to wrap two intermediate layers 68 and 66 therebetween. One variation may be realized by return weaving a small segment at the distal end of one of the uppermost layer 62 or the intermediate layer 68 again, so as to wrap an opened edge of the other one of the uppermost layer 62 or the intermediate layer 68 therebetween. In this way, both ends of the stent are completely smooth tips.

Preferably, the stent in the disclosure is in a multi-layer form, so that both ends (especially the proximal end) of the stent may form smooth tips, so as to avoid secondary damage to the blood vessel by an opened edge of a braid.

The stent in the disclosure is described in detail as above by way of examples. It should be understood by those skilled in the art that the above examples are intended to explain advantages of the stent in the disclosure, rather than limiting the scope of the disclosure, and features in an example may be applied to the stent in other examples separately or in combination in an appropriate situation. Apparent variations and modifications made to the stent by those skilled in the art according to contents of the disclosure herein, fall within the scope of the disclosure, as long as they meet the concept of the disclosure.

Stent Kit

Figure 8:
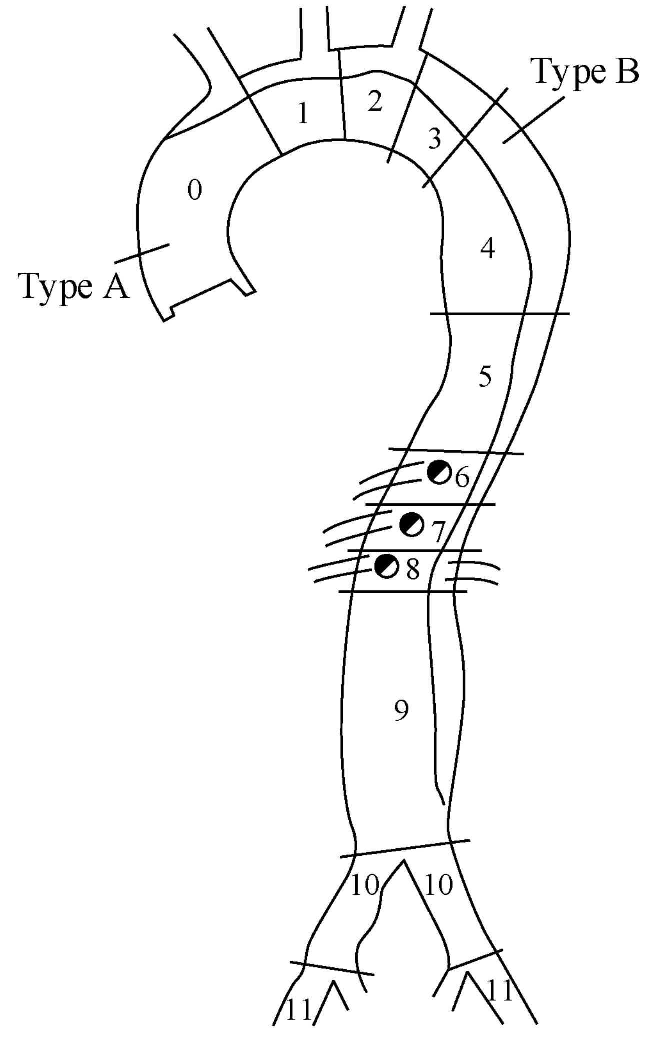
FIG. 8 is a schematic view of an aortic vessel of a person suffering from type A aortic dissection.

The disclosure also provides a stent kit. The stent kit may be used in the entire area from the ascending aorta to the abdominal aorta. With reference to FIG. 8, a schematic view of an aortic vessel is shown. The aorta and the common iliac artery are divided into regions 0-11. Type A aortic dissection is a situation in which a tearing site of an inner wall of the blood vessel is located at region 0 or involves region 0, and type B aortic dissection is a situation in which the tearing sites are located at regions 1-9. FIG. 8 shows type A aortic dissection, in which the vessel intima has been peeled off from region 0 to region 9.

The stent kit in the disclosure includes three stents. A first stent is used in an area from the ascending aorta to the aortic arch, i.e., regions 0-2. A second stent is used in an area of the descending aorta, i.e., regions 3-5. A third stent is used in an area of the abdominal aorta, i.e., regions 5-9. Optionally, the stent kit in the disclosure may further include a stent used for left and right common iliac arteries, i.e., used for region 10.

The three stents for the stent kit may be the stent in the disclosure in any of the embodiments as defined above. For example, the first stent may be the stent shown in FIG. 3, the second stent may be the stent shown in FIG. 1, and the third stent may be the stent shown in A of FIG. 5.

The stent kit in the disclosure may be flexibly combined with stents of different specifications according to the patient's actual needs, thereby providing a more diverse and flexible treatment scheme. Furthermore, each stent has a shorter length, so that the stent is easier to be operated and perform a surgery.

According to an embodiment, distal ends of the first and second stents may be provided with burrs to reduce the thickness of the stents. Meanwhile, the distal end of the first stent is placed inside a proximal end of the second stent, and the distal end of the second stent is placed inside a proximal end of the third stent, thereby avoiding damage to vascular tissues by the burrs.

Conventionally, the first stent may have a diameter of 38-60 mm and a length of 8-11 cm, the second stent may have a diameter of 25-35 mm and a length of 15-20 cm, and the third stent may have a diameter of 20-30 mm and a length of 15-20 cm.

Stent Delivery System and Stent Placement Method

The disclosure also provides a stent delivery system. In the delivery system, the above-mentioned stent in the disclosure is assembled in the system in a delivery configuration, and both ends of the stent are constrained, and the constraints are removed only after other portions of the stent are released, thereby allowing the stent to be completely released.

Figure 9:
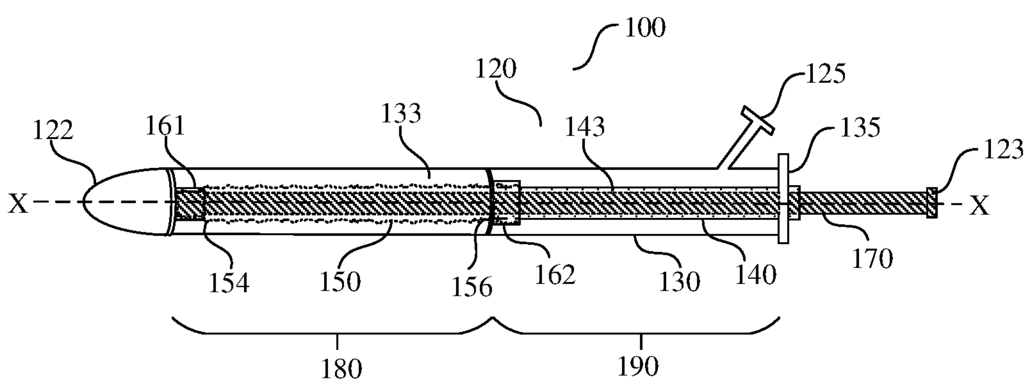
FIG. 9 shows a stent delivery system according to the disclosure.

With reference to FIG. 9, a schematic view of a stent delivery system 100 according to the disclosure is shown. The stent delivery system 100 includes a delivery catheter 120 and a stent 150.

The delivery catheter 120 includes an outer catheter 130, an inner catheter 140 and a push rod 170, which are arranged coaxially with each other and sequentially arranged from exterior to interior of the delivery catheter along a longitudinal axis X-X. The delivery catheter 120 is provided with a distal end 123 and a proximal end 122. The delivery catheter 120 is further provided with a hemostatic valve 125. The outer catheter 130 is provided with a proximal end portion 180 and a distal end portion 190, and a first hollow cavity 133 penetrates through the entire outer catheter 130. The inner catheter 140 is arranged coaxially with the outer catheter 130 along the longitudinal axis X-X and arranged in the first hollow cavity 133 at the distal end portion 190 of the outer catheter, and the inner catheter is provided with a second hollow cavity 143. The push rod 170 extends in the first hollow cavity 133 of the outer catheter 130 and extends through the second hollow cavity 143 of the inner catheter 140, until extending beyond a port 135 of the distal end of the outer catheter. The push rod 170 may be provided with a third hollow cavity (not shown) for passage of a guide wire.

At the proximal end portion 180 of the outer catheter 130, the stent 150 is releasably maintained in the first hollow cavity 133 arranged between the push rod 170 and the outer catheter 130 in a delivery configuration. A first constraint component 161 constrains a proximal end 154 of the stent 150 at a proximal end of the push rod 170. The first constraint component 161 may be a conventional stopper which may be removed from the stent 150 if necessary, thereby allowing the proximal end 154 of the stent 150 to be released. A second constraint component 162 constrains a distal end 156 of the stent 150 at a proximal end of the inner catheter 140. Similarly, the second constraint component 162 may be a conventional stopper which may be removed from the stent 150 if necessary, thereby allowing the distal end 156 of the stent 150 to be released.

Figure 10:
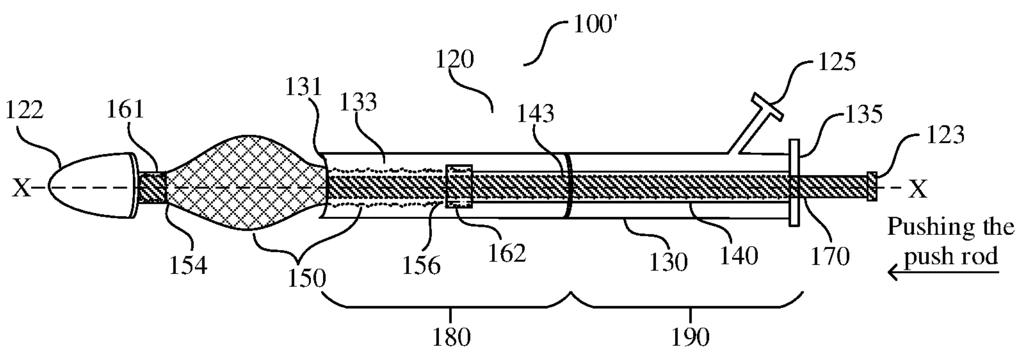
FIG. 10 is a schematic view of the stent delivery system shown in FIG. 9 in a semi-release state.

With reference to FIG. 10, a stent delivery system 100' shown in FIG. 1 in a semi-release state is shown. In FIG. 2, a proximal end 131 of the outer catheter 130 in the delivery system 100' may be separated from the proximal end 122 of the delivery catheter 120, and the outer catheter 130 may be moved relative to the inner catheter 140 and the push rod 170 by pushing the push rod 170 toward the proximal end while maintaining the outer catheter stationary (or, by pulling the outer catheter 130 toward the distal end while maintaining the inner catheter and the push rod stationary).

In the system 100' shown in FIG. 10, by pushing the push rod 170 toward the proximal end 122, the proximal end 122 of the delivery catheter 120 drives the push rod 170 fixedly connected thereto and the stent 150 constrained together with an end of the push rod 170 and the inner catheter 140 constrained together with the stent 150 to move toward the proximal end relative to the outer catheter 130. In this way, the stent 150 starts to be released from the proximal end 154 thereof.

Since the proximal end 154 of the stent 150 is constrained during release, the released segment does not reach its diameter in the natural release state, so that the stent is not contact with the vessel wall. On the one hand, it is conducive to adjusting the position of the stent, and on the other hand, the stent 150 may also be withdrawn into the outer catheter 130 again, and then the stent 150 is released again after its position is adjusted. Furthermore, the proximal end 154 of the stent 150 is constrained, which is also conducive to reducing the friction during initial release and conducive to a stable release. This is particularly important for the surgery that is remotely performed in a narrow blood vessel.

The stent delivery system in the disclosure is particularly advantageous for the treatment of type A aortic dissection.

Figure 11:
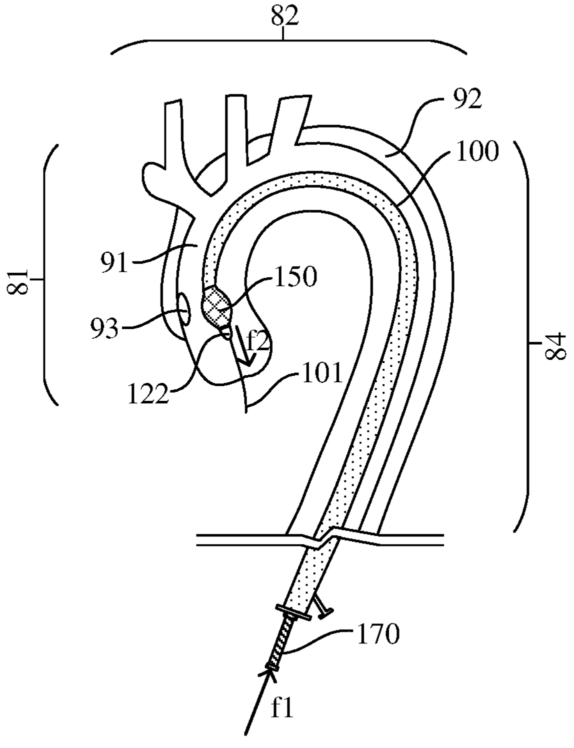
FIG. 11 is a schematic view of placing a stent in type A aortic dissection lesion by using a stent delivery system according to the disclosure.

With reference to FIG. 11, a schematic view of placing a stent 150 in type A aortic dissection lesion by using the stent delivery system 100 in the disclosure is shown, in order to explain the therapeutic advantages of the stent delivery system in the disclosure on type A aortic dissection. FIG. 11 shows that there is a tear 93 in an ascending aorta 81. Thus, a false lumen 92 is formed from the ascending aorta 81, through an aortic arch 83 to a descending aorta 84. The stent delivery system 100 in the disclosure has been guided into a true lumen 91 of the aorta by a guide wire 101. When the stent 150 starts to be released, the operator pushes the push rod 170 in a direction toward the proximal end, where the pushing force is indicated by f1, and the direction of the pushing force is indicated by an arrow directed upward along the descending aorta. The pushing force f1 is transmitted to the proximal end 122 of the delivery catheter along the push rod 170. In this case, since the delivery system 100 turns nearly 180° after passing through the aortic arch 83, a force f2 acting on the proximal end 122 of the delivery catheter has a direction nearly opposite to a direction of the pushing force f1 (as indicated by the arrow). This causes difficulty in controlling a magnitude of the pushing force required during initial release of the stent. In the stent delivery system 100 in the disclosure, with reference to FIG. 11, the proximal end of the stent 150 is temporarily constrained at the proximal end of the push rod 170 by a member, such as a stopper, thereby significantly reducing an outward expansion force of the stent 150 at the proximal end, and reducing the friction between the stent 150 and an inner wall of the outer catheter 130. Therefore, the pushing force required when the stent is initially released by the delivery system 100 in the disclosure is significantly reduced, and the proximal end of the push rod 170 may be easily pushed out of the outer catheter 130.

Figure 12:
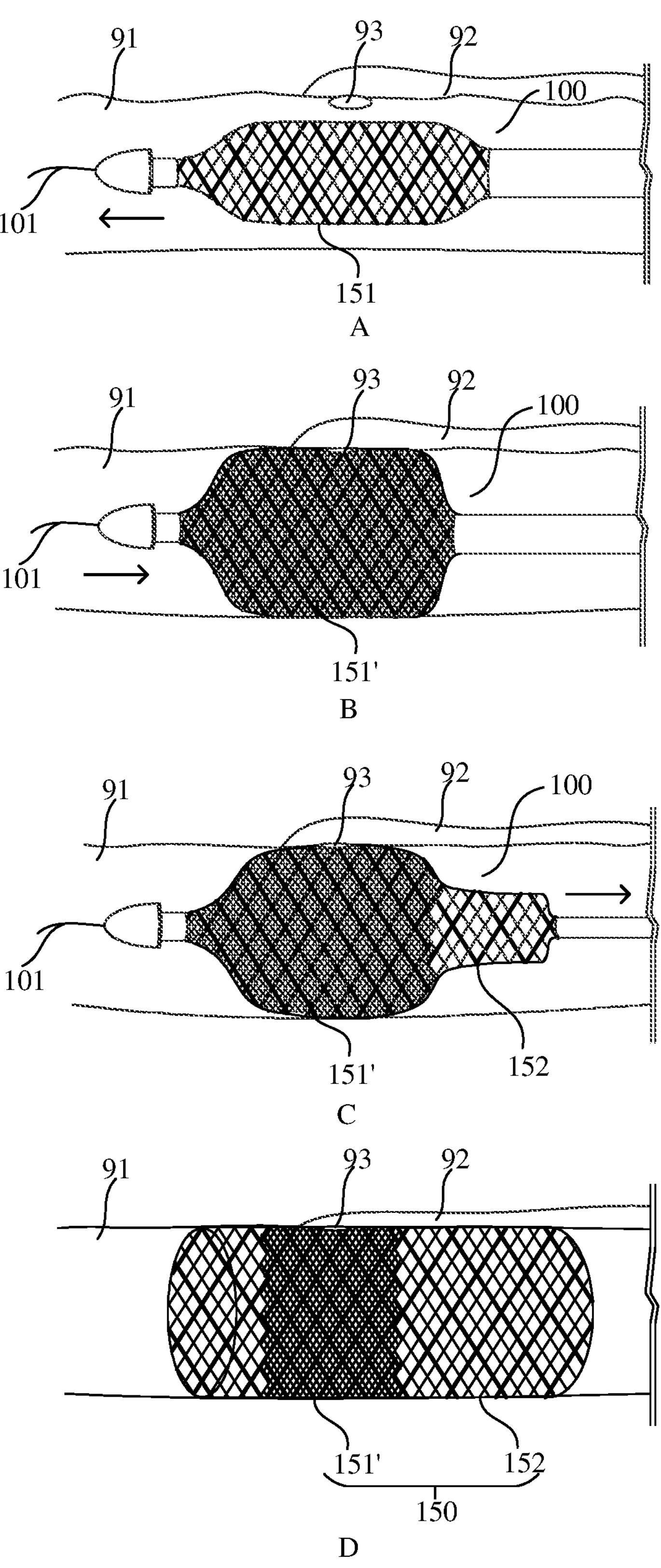
FIG. 12 is a schematic view of placing a stent at a tear of an aortic intima by using a stent delivery system according to the disclosure.

With reference to FIG. 12, a schematic view of placing a stent at a tear of an aortic intima by using a stent delivery system in the disclosure is shown. A segment of aortic vessel 91 including a tear 93 of the vessel intima is shown in A in FIG. 12. Tearing of the intima is induced by the tear 93 to form a false lumen 92. The stent delivery system 100 in the disclosure has been guided to the tear 93, and has released a segment 151 of the stent by pushing the push rod in a direction indicated by the arrow in a case that a position of the outer catheter 130 remains unchanged. With reference to B in FIG. 12, positions of the inner and outer catheters of the delivery system 100 remain unchanged, and the push rod is pulled back in a direction of the arrow in this figure, so that the released segment 151 of the stent is compressed back and finally abuts against a blood vessel area where the tear 93 of the vessel intima is located, thereby forming a compressed segment 151'. When the stent is designed, the diameter of the stent is usually designed to be slightly greater than the diameter of the blood vessel at the placement site, so that the compressed segment 151' abuts tightly against an inner wall of this segment of the blood vessel, obstructs the tear 93, and expands a true lumen of this segment of the blood vessel. The compressed segment 151' remains in this segment of the blood vessel in the compressed shape, since the compressed segment is subjected to an inward contraction force of the vessel wall.

Next, as shown in C in FIG. 12, the remaining segment 152 of the stent is further released by pulling the outer catheter 130 toward the distal end in a direction indicated by the arrow in this figure (the inner catheter 140 and the push rod 170 remain stationary). Finally, after the stent 150 is completely released, constraints of stoppers on both ends of the stent are removed, so that the entire stent 150 is released to the treatment site. Then the delivery catheter is withdrawn from the blood vessel (see D in FIG. 12). The stent 150 placed at the lesion site is provided with two segments, one is the compressed segment 151', and the other is a natural release segment 152. The compressed segment 151' provides functions of obstructing the tear 93 and providing a relatively strong radial support to the blood vessel. The natural release segment 152 provides a function of supporting other parts of the blood vessel properly, and does not hinder the blood flow, and in particular does not hinder the blood flow toward the branch vessel.

According to the disclosure, after the segment 151 of the stent is released (i.e., a state shown in A in FIG. 12), the position of the stent may be confirmed, so that the tear 93 may be accurately obstructed by the compressed segment. If the position is not ideal enough, adjustment may be performed, or even the released segment 151 is withdrawn into the outer catheter again, and is re-released after the position of the delivery system is adjusted.

Likewise, the position of the stent may be confirmed after any segment is released, so as to achieve a best placement effect. Finally, the position of the stent is reconfirmed before the constraints on both ends of the stent are removed, since the stent may be withdrawn and rereleased when its placement position is found to be not ideal at this time. After the constraints on both ends of the stent are removed, the position of the stent cannot be adjusted.

Furthermore, other segments of the stent are compressed in a similar manner to that shown in B in FIG. 4. For example, when a front portion of the stent is released and has abutted against the vessel wall, a segment of the stent continues to be released. Since an end of the subsequently released stent is constrained by the outer catheter, the push rod may remain stationary, and the outer catheter and the inner catheter may be moved simultaneously toward the proximal end, so that a new segment of the stent is released. However, a segment of the stent, which has not abutted against the vessel wall yet, is compressed and abuts against the vessel wall, so as to form a segment with a high metal coverage and a high radial support force.

Detailed solutions of the stent delivery system in the disclosure and the method for placing the stent into the blood vessel by using such a system are explained by the above examples. Variations and modifications may be readily made by those skilled in the art based on the above contents, to be adapted to actual application requirements without departing from the spirit of the disclosure, these variations and modifications also fall within the scope of the disclosure.

First Embodiment

This embodiment provides a stent provided with a structure shown in FIG. 1 and used in an area of the descending aorta. The stent is made of a nickel-titanium alloy material, and is formed by interleaving 54 first wires with a diameter of 100 μm and 12 second wires with a diameter of 400 μm. The stent is woven into two layers in a return weaving manner. The return weaving manner is shown in A in FIG. 5. In this figure, the proximal end is a smooth tip which is woven in a return weaving manner. The distal end is two layers of burrs. The burr at the outer side is woven in a return weaving manner by a small segment, so as to place the burr at the inner side inside the segment which is woven in a return weaving manner, thereby preventing the burrs from being exposed to damage the vessel wall.

The stent has a conical shape, and has a diameter of 45 mm at the proximal end, a diameter of 32 mm at the distal end, and a length of 8 cm. A fixed length of this stent after it is released in the blood vessel may be up to 24 cm.

As detected by a scanning electron microscope, a metal coverage of the stent in this embodiment in a natural state is 40%, and a metal coverage of the stent after axial maximum compression is about 90%. As detected by a radial support force tester, a radial support force of a thicker portion of the stent in this embodiment in the natural state is 350 N, and a radial support force of each portion of the stent after the axial maximum compression is greater than 400 N, even greater than 600 N.

In addition, in order to simulate a situation of axial bending stress of the stent when the stent is fixed at the aortic arch, a radial straightening force of the stent is measured between 0.4 N and 1.0 N.

Second Embodiment

This embodiment provides a stent provided with a structure shown in FIG. 3 and used in an area from the ascending aorta to the aortic arch. The stent is made of a nickel-titanium material, and is formed by interleaving 120 first wires with a diameter of 100 μm and 8 second wires with a diameter of 400 μm. The stent is woven into four layers in a return weaving manner. The return weaving manner is shown in C in FIG. 5. In this figure, the proximal end is a smooth tip which is woven in a return weaving manner completely. At the distal end, two layers of burrs are located at the inner side of the stent, and two layers of edges, which are woven in a return weaving manner, are located at the outer side of the stent, thereby preventing the burrs from being exposed to damage the vessel wall.

A portion of the stent corresponding to the ascending aorta has a diameter of 45 mm and a length of 9 cm, and a portion of the stent corresponding to the aortic arch has a diameter of 32 mm and a length of 6 cm. A sparse mesh area is provided at 30 mm from the proximal end of the stent, and the sparse mesh area has a length of 6 cm and an arc length of ⅓ the circumference.

As detected by a scanning electron microscope, a metal coverage of the stent in this embodiment in a natural state is 80% except for the sparse mesh area, and a metal coverage of the stent after axial maximum compression is 98%. As detected by a radial support force tester, a radial support force of a thicker portion of the stent in this embodiment corresponding to the ascending aorta in the natural state is about 400 N, a radial support force of a portion provided with the sparse mesh area is about 100 N, and a radial support force after the axial maximum compression is greater than 400 N, even up to 500 N or more.

In addition, in order to simulate a situation of axial bending stress of the stent when the stent is fixed at the aortic arch, a radial straightening force of the stent is measured between 0.4 N and 1.0 N.

The forgoing is only part of specific embodiments of the disclosure, and thus is not intended to limit the patent scope of the disclosure. Any equivalent structural transformation made by using the description and accompanying drawings of the disclosure within the inventive concept of the disclosure, or directly/indirectly applied to other related technical fields, is included within the patent scope of protection of the disclosure.

What is claimed is:

1. A stent, the stent being used in an aorta, the stent being formed by weaving at least two kinds of wires with different diameters, the at least two kinds of wires comprising first wires and second wires, and the stent being configured to be at least partially compressible and extendable along an axial direction of the stent in a natural release state, wherein a diameter of each of the first wires ranges from 20 μm to 150 μm, and a diameter of each of the second wires ranges from 150 μm to 800 μm;

wherein the second wires comprise two kinds of thick wires with different diameters, the two kinds of wires comprising first thick wires and second thick wires, wherein a diameter of each of the first thick wires ranges from 150 μm to 300 μm, and a diameter of each of the second thick wires ranges from 300 μm to 600 μm;

wherein the stent is formed by weaving 96-202 wires, among which the second wires comprise 6-24 first thick wires and 4-24 second thick wires, and remaining wires are the first wires, provided that a sum of a number of the first thick wires and a number of the second thick wires is less than or equal to 30.

2. The stent according to claim 1, wherein in the natural release state, a metal coverage of the stent is at least 30%, and a radial support force of the stent is greater than or equal to 100 N.

3. The stent according to claim 2, wherein in the natural release state, the metal coverage of the stent ranges from 30% to 90%, and the radial support force of the stent ranges from 100 N to 600 N.

4. The stent according to claim 1, wherein in a release and axial maximum compression state, a metal coverage of the stent is at least 80%, and a radial support force of the stent is greater than or equal to 400 N.

5. The stent according to claim 4, wherein in the release and axial maximum compression state, the metal coverage of the stent ranges from 80% to 100%, and the radial support force of the stent ranges from 400 N to 1000 N.

6. The stent according to claim 1, wherein when the stent is placed in the aorta, the stent has different degrees of compression in the axial direction of the stent.

7. The stent according to claim 1, wherein in the natural release state, a metal coverage of the stent ranges from 30% to 60%, and a radial support force of the stent ranges from 200 N to 600 N.

8. The stent according to claim 7, wherein in a release and axial maximum compression state, the metal coverage of the stent ranges from 80% to 90%, and the radial support force of the stent ranges from 400 N to 1000 N.

9. The stent according to claim 1, wherein in the natural release state, a metal coverage of the stent ranges from 60% to 90%, and a radial support force of the stent ranges from 100 N to 600 N.

10. The stent according to claim 9, wherein in a release and axial maximum compression state, the metal coverage of the stent ranges from 90% to 100%, and the radial support force of the stent ranges from 500 N to 1000 N.

11. The stent according to claim 1, further comprising a sparse mesh area, wherein the sparse mesh area is formed only of the second wires by removing the first wires, and the sparse mesh area is configured to be arranged at branch arteries of a corresponding treatment site after the stent is released.

12. The stent according to claim 1, further comprising a first sparse mesh area and a second sparse mesh area, wherein each of the first sparse mesh area and the second sparse mesh area is formed only of the second wires by removing the first wires, the first sparse mesh area is configured to be arranged at an aortic arch site, and a radian of the first sparse mesh area occupies ⅓-½ circumference of the stent; and the second sparse mesh area is configured to be arranged at a branch artery site in an abdominal aorta, and a radian of the second sparse mesh area occupies ½ circumference of the stent.

13. The stent according to claim 1, wherein the stent is used in the aorta comprising an area of an abdominal aorta, and the stent is internally provided with two common iliac artery stent fixing parts, which are configured to fix a left common iliac artery stent and a right common iliac artery stent.

14. The stent according to claim 13, wherein the two common iliac artery stent fixing parts are arranged inside the stent and correspond to the abdominal aorta close to a bifurcation of left and right common iliac arteries, and the two common iliac artery stent fixing parts are configured as two annuluses tangent to each other and are integrally formed with an inner wall of the stent.

15. The stent according to claim 1, wherein the first wires comprise two kinds of thin wires with different diameters, the two kinds of thin wires comprising first thin wires and second thin wires, wherein a diameter of each of the first thin wires ranges from 20 μm to 100 μm, and a diameter of each of the second thin wires ranges from 100 μm to 150 μm.

16. A stent delivery system, comprising:

a delivery catheter, the delivery catheter comprising an outer catheter, an inner catheter and a push rod, wherein the outer catheter, the inner catheter and the push rod are arranged coaxially with one another and arranged sequentially from exterior to interior of the delivery catheter, wherein the outer catheter is provided with a proximal end portion and a distal end portion, and the outer catheter is provided with a first hollow cavity penetrating through the outer catheter;

wherein the inner catheter extends in the first hollow cavity at the distal end portion of the outer catheter, and the inner catheter is provided with a second hollow cavity penetrating through the inner catheter; and wherein the push rod extends through the first hollow cavity of the outer catheter and the second hollow cavity of the inner catheter, and extends out of a distal end of the inner catheter; and a stent, the stent being releasably maintained between the push rod and the outer catheter in a delivery configuration and being arranged in the first hollow cavity at the proximal end portion of the outer catheter, the stent being used in an aorta, the stent being formed by weaving at least two kinds of wires with different diameters, the at least two kinds of wires comprising first wires and second wires, and the stent being configured to be at least partially compressible and extendable along an axial direction of the stent in a natural release state, wherein a diameter of each of the first wires ranges from 20 μm to 150 μm, and a diameter of each of the second wires ranges from 150 μm to 800 μm, wherein the delivery catheter is configured so that the outer catheter, the inner catheter and the push rod are axially movable relative to one another, and one end of the stent is removably constrained to a proximal end of the push rod, and another end of the stent is removably constrained to a proximal end of the inner catheter;

wherein the second wires comprise two kinds of thick wires with different diameters, the two kinds of thick wires comprising first thick wires and second thick wires, wherein a diameter of each of the first thick wires ranges from 150 μm to 300 μm, and a diameter of each of the second thick wires ranges from 300 μm to 600 μm;

wherein the stent is formed by weaving 96-202 wires, among which the second wires comprise 6-24 first thick wires and 4-24 second thick wires, and remaining wires are the first wires, provided that a sum of a number of the first thick wires and a number of the second thick wires is less than or equal to 30.

* * * * *